United States Patent [19]

Castellana

[11] Patent Number: 5,599,289
[45] Date of Patent: Feb. 4, 1997

[54] MEDICAL DRESSING WITH SEMI-PERIPHERAL DELIVERY SYSTEM

[75] Inventor: Frank S. Castellana, Princeton, N.J.

[73] Assignee: Bristol-Myers Squibb Co., Skillman, N.J.

[21] Appl. No.: 368,734

[22] Filed: Jan. 4, 1995

Related U.S. Application Data

[63] Continuation of Ser. No. 95,121, Jul. 20, 1993, abandoned.

[51] Int. Cl.⁶ .............................. A61F 13/00; A61F 15/00
[52] U.S. Cl. .............................. 602/57; 602/58; 128/888; 128/853
[58] Field of Search .............................. 602/41, 42, 48, 602/51, 57, 58, 59; 128/851, 853, 854, 887, 888; 604/307; 206/440, 441

[56] References Cited

U.S. PATENT DOCUMENTS

| | | |
|---|---|---|
| Re. 33,353 | 9/1990 | Heinecke . |
| 4,372,303 | 2/1983 | Grossmann et al. ............ 128/851 |
| 4,485,809 | 12/1984 | Dellas ............................ 602/52 |
| 4,513,739 | 4/1985 | Johns . |
| 4,600,001 | 7/1986 | Gilman ........................... 602/57 |
| 4,664,106 | 5/1987 | Snedeker ....................... 602/57 |
| 4,706,662 | 11/1987 | Thompson . |
| 4,753,232 | 6/1988 | Ward ............................. 602/57 |
| 4,787,380 | 11/1988 | Scott . |
| 4,917,112 | 4/1990 | Kalt . |
| 4,917,928 | 4/1990 | Heinecke . |
| 4,941,882 | 7/1990 | Ward et al. ..................... 604/305 |
| 5,088,483 | 2/1992 | Heinecke . |
| 5,099,832 | 3/1992 | Ward . |
| 5,152,282 | 10/1992 | Elphick et al. ................. 602/58 |
| 5,153,040 | 10/1992 | Faasse, Jr. . |
| 5,160,315 | 11/1992 | Heinecke et al. .............. 602/57 |
| 5,449,340 | 9/1995 | Tollini ........................... 602/57 |

FOREIGN PATENT DOCUMENTS

| | | |
|---|---|---|
| 0051935 | 3/1990 | European Pat. Off. . |
| WO9212757 | 11/1992 | WIPO . |

*Primary Examiner*—Paul B. Prebilic
*Attorney, Agent, or Firm*—Theodore R. Furman, Jr.; John M. Kilcoyne

[57] ABSTRACT

In accordance with the present invention novel medical dressing systems and methods are disclosed using a semi-peripheral support design which provides at least one conformal, unsupported dressing edge upon application. The dressing system disclosed herein comprises a backing layer, an adhesive material overlying the backing layer and a release liner overlying the adhesive, wherein said medical dressing system further comprises a final dressing portion and a semiperipheral support portion partially surrounding said dressing portion and said support portion being partially defined by a separation, said dressing portion being further defined by at least one unsupported edge, said one or more unsupported edges extending from a first end to a second end of said semiperipheral support portion.

18 Claims, 3 Drawing Sheets

MEDICAL DRESSING WITH SEMI-PERIPHERAL DELIVERY SYSTEM

This is a continuation of application Ser. No. 08/095,121 filed Jul. 20, 1993, entitled Medical Dressing with Semi-Peripheral Delivery System and Methods Therefor, now abandoned.

FIELD OF THE INVENTION

The present invention relates to medical dressings and, more particularly, to medical dressings having delivery systems for facilitating handling and application of the dressings and to methods therefor.

BACKGROUND OF THE INVENTION

Medical dressings are popular for use on anatomical wounds to protect the wounds and promote healing, at catheter sites to secure and stabilize the catheters, as surgical drapes to define a sterile field and in diverse medical procedures to perform various other functions. Many medical dressings are of minimal thickness to provide great flexibility allowing the dressings to flex and conform to the irregular shapes and contours of anatomical and other surfaces to which they may be applied and to permit moisture to penetrate the dressings to prevent maceration of the skin. Such dressings typically include a thin backing sheet or film, a layer, surface, or body of adhesive carried by the backing sheet and a removable release liner disposed over the adhesive. Upon removal of the liner, the dressing is flexible, conformable, supple, limp or flimsy due to the minimal thickness thereof such that there is a tendency for the dressing to wrinkle, buckle, fold or turn over on itself. Accordingly, handling of the dressing and application of the dressing to a surface can be difficult, tedious and can result in portions of the dressing becoming stuck together or the dressing being improperly applied.

Various delivery systems for medical dressings have been proposed to facilitate handling and application of the dressings. Many proposed delivery systems are part of the medical dressings themselves, and U.S. Pat. Nos. 4,413,621 to McCracken et al, 4,485,809 to Dellas, 4,664,106 to Snedeker, 5,160,315 to Heinecke et al and RE 33,353 to Heinecke and European Patent 0,051,935 are illustrative of such medical dressing delivery systems. Some of the disadvantages of prior art medical dressing delivery systems include complexity, increased number of parts, increased material and manufacturing costs, intricate handling and application protocols, the need for multiple release liners and touching of or other contact with the adhesive during handling and/or application with concomitant impairment of cleanliness and adhesion. Some prior art medical dressing delivery systems utilize a release liner having a central window portion and a continuous outer frame portion with the central window portion being removable separately from the backing sheet to expose a face of the backing sheet carrying the body of adhesive. Upon removal of the central window portion, the support portion remains attached to the backing sheet to rigidify and support the dressing and prevent or minimize wrinkling, folding and buckling of the dressing during handling and application of the dressing on a surface. Once the dressing has been applied to the surface by placing the exposed face of the backing sheet thereagainst, the support portion is detached or removed, with or without a section of the backing sheet, to complete the application.

A major disadvantage is that there is no edge portion of such dressings which has the desired conformability of the dressing itself due to the intentional rigidity of the continuous frame. For example, the design in EP 51,935 provides a second release liner overlying the backing layer wherein the second release liner is defined by a central window and a frame. A first release liner overlying the skin-contacting adhesive surface can be removed as well as the central window portion of the second release liner prior to application. However, the caregiver typically touches part of the skin-contacting region during application and therefore cleanliness is compromised. Also, since the frame intentionally provides a more rigid periphery, the conformal nature of the dressing, especially when being used over a catheter entry point, is decreased. That is, the continuous frame makes it difficult to secure the dressing sealably around the catheter. Further, the caregiver is unable to see all that is being covered by the final dressing since the frame covers the periphery of same.

Another continuous periphery or "window frame" design is disclosed in U.S. Pat. No. 4,485,809 to Dellas. The '809 patent utilizes only the release liner which overlies the skin-contacting adhesive surface and which includes a central window portion and a continuous peripheral frame portion. The dressing further includes perforations in the dressing backing and adhesive in alignment with the central window portion. Upon removal of the central window portion of the release liner, the dressing is applied and the frame and continuous peripheral portion of the dressing itself are removed by tearing at the perforations. This design still suffers from a lack of conformability of at least one edge for sealing a catheter site and also requires a considerable force and tugging to begin the periphery removal. Periphery removal for such a continuous frame design can cause edge roll-up and dressing shift or displacement

SUMMARY OF THE INVENTION

In accordance with the present invention, novel medical dressing systems and methods are disclosed using a semi-peripheral support design which provides at least one conformal, unsupported dressing edge upon application. The dressing system disclosed herein comprises a backing layer, an adhesive material overlying the backing layer and a release liner overlying the adhesive, wherein said medical dressing system further comprises a final dressing portion and a semiperipheral support portion partially surrounding said dressing portion, said support portion being partially defined by a separation line, and being further defined by at least one unsupported edge, said one or more unsupported edges extending from a first end to a second end of said semiperipheral support portion.

DETAILED DESCRIPTION OF THE PREFERRED EMBODIMENTS

Figure 1:
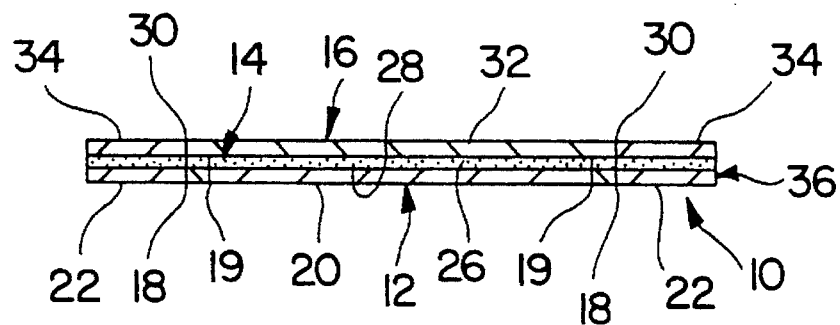
FIG. 1 is a sectional view taken along line 1—1 of FIG. 2.

The present semiperipheral delivery system provides an excellent mechanism for application of thin medical films with support sufficient to prevent film folding and sticking, while providing at least one unsupported, and therefore conformal, final dressing edge during application. Further, with the present system the caregiver can visualize the entire final dressing area during application and caregiver contact to the final dressing adhesive is avoided. Typical thin film dressings include a backing, an adhesive and a release liner. This invention discloses a system (and methods for using same) wherein a final dressing portion is that backing and adhesive portion of the system which remains on the patient, i.e., after removal of support and/or delivery systems. Herein, the final dressing portion is defined in part by a semiperipheral portion of backing, adhesive and liner which partially surrounds, and is separable from, the final dressing portion, and is further defined by one or more unsupported, conformal edges. A separation line distinguishes the removable semiperipheral portion from the final dressing portion and the separation line can be any convenient configuration for providing selective removal of release liner from final dressing adhesive area, and separation of the so-exposed final dressing from the semiperipheral portion. Preferably the separation line consists of a cut line in the release liner and perforations through the adhesive and backing wherein the positioning of the perforations are in the vicinity of the cut line. In a preferred embodiment the perforations and cut line are in substantial alignment and most preferred is where the perforations are slightly inward of the cut line.

In addition to the above advantages of conformability and sealability about a catheter and catheter entry site, the one or more unsupported conformal edges common to both the "as applied" and final dressings provide an additional benefit not found in the prior art. The prior art window frame/perforation designs suffer from the fact that all of the edges are pulled, stretched, lifted or otherwise deformed during support frame removal, especially upon initiation of removal. The one or more unsupported edges of the present system are free, unsupported, leading edges in their as-applied state. Once applied, they are not subsequently disturbed by any of the support portion removal steps. This is believed to provide enhanced adhesive stability in that the one or more initially applied edges provide somewhat of an anchor. Clearly, the number of edges for which semiperipheral support material has to be removed is also decreased in the present case. Thus, better adhesion with less edge roll-up is achieved.

Generally, in practice, the inner selectively removable release liner which overlies the final dressing adhesive is removed, typically by a slight bending of the dressing system at the cut line. The balance of the release liner remains on the semiperipheral portion and provides support of the thin film during application. Since the semiperipheral portion does not completely surround the final dressing portion one or more final dressing edges are unsupported and are capable of being secured conformally and securely to the patient and/or catheter without interference from the more rigid release liner, simultaneously with the support being provided. The ability to provide a thin film dressing which is supported and which concurrently has one or more conformal edges provides that a much improved and much simpler process in which a larger percentage of the dressing and dressing edges are finally secured while in a supported state as compared to the prior art.

The semiperipheral portion is removable simply and with less force since either end of the semiperipheral portion can be grasped and pulled lightly. The present dressing application and support removal are easily carried out with only one hand leaving the other hand free for other uses, i.e., catheter support, etc.

Figure 2:
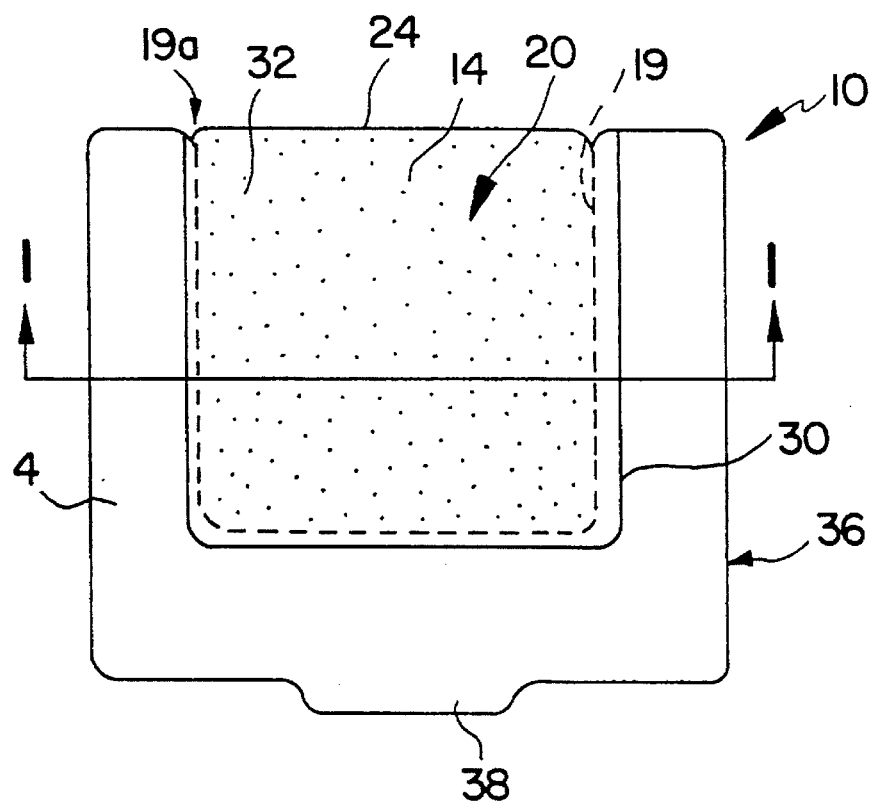
FIG. 2 is a top plan view of a medical dressing with semi-peripheral delivery system according to the present invention.

A medical dressing with semi-peripheral delivery system according to the present invention is illustrated at 10 in FIGS. 1 and 2. As shown in FIG. 1, the medical dressing with semi-peripheral delivery system 10 includes a backing sheet or film 12, a layer, body or surface of adhesive 14 carried by backing sheet 12 and a release liner 16 releasably secured over the skin-contacting surface of adhesive 14. Backing sheet 12 is preferably made of a thin, flexible, conformable, resilient, supple, limp or flimsy material that can flex or bend to conform to irregular surfaces or contours, such as those of anatomical body parts, of a dressing receiving surface to which the medical dressing may be applied, the medical dressing typically being applied to an anatomical skin surface. Preferably, backing sheet 12 is resilient enough to stretch or flex in response to movement or flexing of the dressing receiving surface and to conform to the dressing receiving surface when the dressing receiving surface returns to an unflexed condition. Backing sheet 12 is preferably transparent to permit visualization of the dressing receiving surface, or the backing sheet can be opaque. The backing sheet 12 can be air permeable to allow oxygen to penetrate the dressing as well as moisture vapor permeable to allow moisture from the skin surface to escape through the dressing, and the backing sheet can be liquid, air and bacteria impermeable. Non limiting examples of materials suitable for backing sheet 12 include polymeric materials, such as polyurethane, copolyester, elastomeric polyester, polyethylene, blends of polyurethane and polyester, chlorinated polyethylene, styrene/butadiene block copolymers and polyvinyl chloride, formed into continuous films or sheets by casting, extrusion or other processes. Backing sheet 12 can have various sizes and configurations dependent on the surfaces to which the dressing is to be applied; and, as shown in FIGS. 1 and 2, backing sheet 12 has a square peripheral configuration with rounded or radiused corners. The backing sheet 12 preferably has a minimal thickness, typically in the range of 0.0005 inch to 0.004 inch, preferably about 0.0015 inch, with conformability of the dressing increasing with decreasing thickness of the backing sheet.

The dressing system shown in FIG. 1 has a separation line 18 which generally defines the area where an initially removable liner portion 32 of the release liner 16 is selectively removed from the adhesive 14, and where the semiperipheral support portion 36 is separable from the final dressing potion 20. The separation line 18 can be any convenient arrangement for providing these requirements but typically comprises perforations 19 through the backing 12 and adhesive 14 defining the final dressing 20, and a cut line 30 through the release layer 16 defining portion 32 and in substantial alignment with perforations 19.

In FIG. 2, release liner portion 17 has been removed to expose the skin contacting surface of adhesive 14. As shown in FIG. 2, the semiperipheral support portion 36, comprising a semiperipheral portion 34 of the release liner 16, adhesive 14 and backing 12, defines part of the periphery of final dressing 20. Final dressing 20, of course, comprises adhesive 14 and backing 12, and is separable from the semiperipheral portion 34 by perforations 19 and is further defined by unsupported edge 24. Preferably, as shown in FIG. 2, the region where the first and second ends of the semiperipheral portion 36 intersect the (one or more) unsupported edge(s) 24 at the initiation or ending point of perforation 19 is defined by a recess, V-groove or cut-out 19a to further facilitate support removal with decreased force or pulling. Also as shown in FIGS. 1 and 2, the perforations 19 are slightly inward of the cut line 30 to avoid premature separation of the semiperipheral portion 36 from the final dressing portion 20 upon selective removal of release liner portion 32.

The cut line 30 is preferably a kiss cut extending through the release liner 16 only. Perforations 19, as understood by those skilled in the art, are a series of individual perforations separated by bridges of material therebetween. The length and depth of the perforations and/or bridges can be selected in accordance with desired ease of, or resistance to, separation taking into account the thickness of materials in the dressing system, the tenacity of adhesion between the adhesive 14 and release liner 16, and the like. While not intended to be limiting, a suitable range for bridges of material is from about 0.010 to about 0.060 inches with a preferred range being from about 0.020 to about 0.050 inches, with about 0.040 inches being most preferred. Non-limiting suitable ranges for perforations are from about 0.030 to about 0.250 with from about 0.160 to about 0.200 inches being preferred.

Adhesive 14 is provided on a skin contacting side or face 26 of backing sheet 12 to cover at least the entire area circumscribed by the final dressing portion 20 and, preferably, for ease of manufacturing adhesive 14 covers the entire area of face 26 of backing 12 including the peripheral backing portion 22. Body of adhesive 14 can be provided on face 26 in many various ways including solvent spreading, coating and extrusion, for example, and the adhesive can be applied directly to backing sheet 12 or indirectly via a carrier sheet. The adhesive utilized is preferably a pressure-sensitive, skin contact adhesive that is preferably hypo-allergenic and non-irritating to skin. Some materials suitable for body of adhesive 14 include acrylate copolymers, such as copolymers of 2-ethylhexylacrylate and vinyl acetate with or without a cross-linking agent, water based adhesives and hot melt adhesives, for example. If desired, various medicaments or antimicrobial agents can be included in the adhesive to promote healing and inhibit infection. The adhesive is preferably applied on face 26 in a thin layer, such as on the order of 0.001 inch to 0.010 inch in thickness or greater (according to the desired application), sufficient to obtain adequate skin adhesion without impairing the air and moisture vapor transmission characteristics of the dressing.

Preferably, the adhesive 14 is a polyurethane adhesive. A non-limiting example such a class of adhesives are those polyurethane adhesives disclosed in European Application No. 93308847.8 having a priority date of Nov. 9, 1992 entitled "POLYURETHANE PRESSURE SENSITIVE ADHESIVES".

These novel pressure sensitive adhesives comprise a polyurethane polymer having excess hydroxyl functionality, a glass transition temperature of less than about 0° C., a moisture vapor transmission rate of at least about 300 grams/meter$^2$/24 hours measured at 37° C. with a 90% relative humidity gradient, and a peel adhesion to human skin of between about 0.5 and 3.5 newtons/cm width of the polymer. Advantageously, the glass transition temperature is less than about −30° C., the moisture vapor transmission rate is at least about 500 grams/meter$^2$/24 hours, and the peel adhesion is between about 0.8 and 3 newtons/cm width of the polymer. If desired for the particular end use of the adhesive, the polymer can be made to possess a moisture absorption at equilibrium of at least about 20% of its weight.

Preferably, the polyurethane polymer is formed by the reaction of an isocyanate component and a polyol component at a molar ratio of isocyanate moieties to hydroxyl moieties of less than one with at least one of the components having a functionality that is greater than two to facilitate crosslinking. The polymer is crosslinked to a crosslink density alpha ($\alpha$) defined by the equation $$\alpha = \frac{\sum_{n}^{i=1} Xi(Fi-2)}{(1.05-r)Mw}$$

wherein i=1 to n where n is the number of the reactant components;

Xi=mole fraction of i$^{th}$ component;

Fi=functionality of the i$^{th}$ component;

r=the NCO/OH molar ratio;

Mw=Molecular weight of the polyol;

of between about 2×10$^{-4}$ and 10×10$^{-4}$ to obtain the desired properties. When the isocyanate component is an aliphatic polyisocyanate, the crosslink density is between about 2×10$^{-4}$ and 9×10$^{-4}$, while for aromatic polyisocyanates the crosslink density is between about 4×10$^{-4}$ and 9×10$^{-4}$.

A preferred molar ratio is between about 0.5 and 0.99, and more preferably between about 0.65 and 0.95. The polyol component advantageously comprises a polyether polyol having a molecular weight of between about 1,000 and 10,000, such as a homopolymer or copolymer containing ethylene oxide or propylene oxide groups. The polyol component may also be a hydroxyl terminated prepolymer. When moisture absorbent adhesives are desired, the polyol component can be a polyether diol or triol containing at least about 30% by weight of ethylene oxide groups.

The isocyanate component has a functionality equal to or greater than 2 and may be an aliphatic polyisocyanate, an aromatic polyisocyanate or combinations thereof. Also, the isocyanate component may be an isocyanate terminated prepolymer. As noted, at least one of the isocyanate or polyol components must have a functionality of greater than 2 to obtain the desired crosslinking of the polymer.

Release liner 16 is made up of a sheet of material detachably secured over or held by body of adhesive 14 to protect and prevent contact with the body of adhesive prior to use. Release liner 16 has a surface 28 in contact with or releaseably adhered to body of adhesive 14, the surface 28 having an area to cover the body of adhesive in its entirety or substantially in its entirety. As shown in FIGS. 1 and 2, the release liner 16 has a surface area equal to the surface area of the backing sheet and a periphery aligned with the backing sheet periphery of the final dressing 20 and semiperipheral portion 34 in their pre-separated state. However, the release liner can have a surface area greater or less than the surface area of the backing sheet if so desired. Release liner 16 is cut or severed along a cut line 30 dividing the release liner into the initially removed portion 17 and the semi-peripheral liner 33.

The actual width of the semiperipheral support portion 36 depends upon the thickness of the film/adhesive dressing, the rigidity of the release liner material and the size of the dressing area. For thin film dressings on the order of 0.5 to about 10 mils in thickness and having an area of from about 5 to about 25 square inches, the semiperipheral portion can be conveniently selected from about 0.25 to about 0.75 inches in width depending upon the release liner material.

As illustrated in FIG. 1, an optional handling tab 38 may be incorporated into the design and is provided along the semiperipheral portion 36, either partially or diametrically opposed to the unsupported edge 24. Handling tab 38 can be provided on the backing sheet 12, the release liner 16, or both, the tab 38 being defined by an integral extension or projection of the semi-peripheral support portion 36. The body of adhesive 14 preferably extends between the extensions of the liner and backing such that the extensions adhere to one another. As shown in FIG. 1, the handling tab 38 has a truncated triangular configuration and is arranged near the center of the side opposite edge 24; however, the handling tab can have various other configurations and arrangements. Also, the location can be as desired and more than one handling tab can be provided.

Various materials can be utilized for the release liner 16 including conventional smooth surface paper materials, polyester films and polyolefin films of the type typically utilized as release liners, such as, for example, kraft paper, polyethylene, polypropylene, polyester and composites thereof. Release liner 16 is sufficiently thick, i.e., on the order of 0.004 inch to 0.0075 inch in thickness or higher, to rigidify backing sheet 12 prior to use. The release liner is preferably sufficiently rigid and/or thick to normally maintain a flat configuration; however, the release liner can have some flexibility to bend, flex or deform in response to external pressure. Depending on the material utilized for release liner 16, the surface 28 can be coated with a release agent, such as fluorochemicals or silicone, for example, to facilitate release of liner portion 32 from the adhesive 14 of the final dressing portion 20. It will be appreciated that the material utilized for release liner 16, with or without a release agent, can be varied to achieve a desired bond or tenacity of adhesion between the release liner and the body of adhesive and that the bond or tenacity of adhesion can be selected such that manual removal or peeling away of the liner portion 32 from the backing sheet can be accomplished with a gentle pressure or pulling force and without damage to or impairment of the dressing.

According to one embodiment for a rectangular configured dressing, the dressing system has a length of 3.8 inches and a width of 2.6 inches with rounded corners having a radius of 0.60 inch. The final dressing configuration 20 has a length of 3.0 inches and a width of 2.0 inches with the separation line having rounded corners with a 0.20 inch radius. The length of the final dressing portion is disposed along the unsupported edge, and the handling tab has a length of 1.25 inches parallel to the length of the dressing and a width of 0.125 inch. As is understood the dressings of this invention can be of any convenient size, e.g. about 2–6 inches wide and about 14 8 inches long and having a semipipheral support portion about 0.25 to about 0.75 inches wide. Typical dressings can be 2×3 inches, 4×4 inches, 6×8 inches, and the like.

Figure 3:
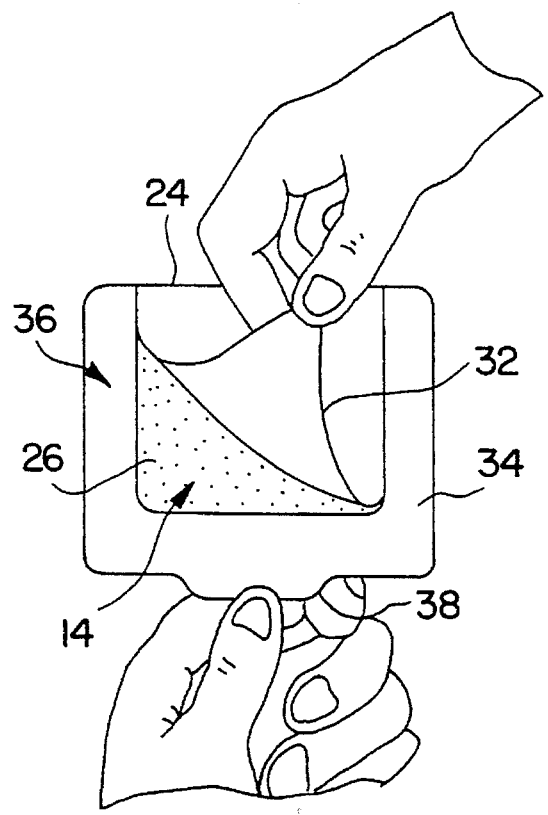
FIG. 3 is a perspective view of the medical dressing with semi-peripheral delivery system of FIG. 1 showing an inner portion of the release liner being removed to expose a face of the skin-contacting adhesive surface.
Figure 4:
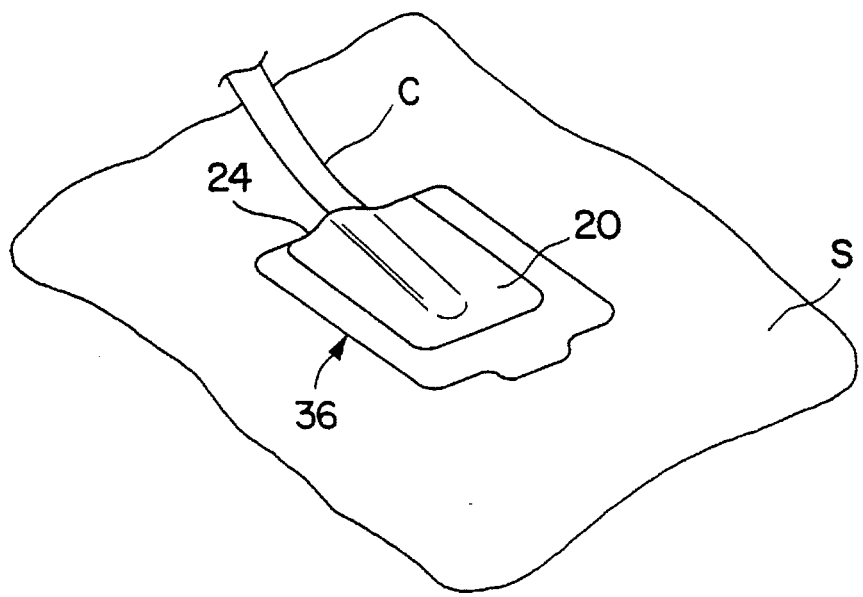
FIG. 4 is a perspective view of the medical dressing with semi-peripheral delivery system of FIG. 1 showing the skin-contacting adhesive surface and the backing sheet adhered to an anatomical skin surface to secure a catheter in place on the surface.
Figure 5:
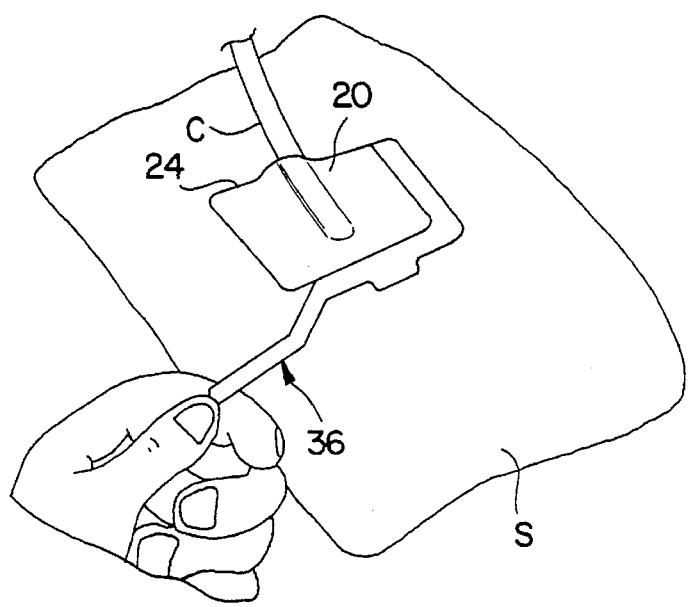
FIG. 5 is a perspective view of the medical dressing with semi-peripheral delivery system of FIG. 4 showing a semi-peripheral segment of the dressing being detached from the remainder of the dressing.

In use, the medical dressing with semi-peripheral delivery system 10 according to the present invention is supplied with the final dressing and semi-peripheral sections 20 and 36 attached to one another and release liner 16 including the removable liner and semi-peripheral support portions 32 and 34 disposed over backing sheet 12 to protect the body of adhesive 14 and prevent contact therewith. With the release liner 16 disposed over backing sheet 12, the dressing can be maintained in a generally flat or wrinkle free condition for ease of packaging in a sterile wrapping or container. In order to apply the dressing to a dressing receiving surface, such as an anatomical skin surface, the dressing is manually grasped with one hand at handling tab 38 and is gently flexed to allow an edge of removable liner portion 32 to be manually grasped with the other hand as shown in FIG. 3. Removable liner portion 32 is removed, released or detached from backing sheet 12 by manually lifting, pulling or peeling away the removable liner portion 32 from the backing sheet 12. Upon removal of liner portion 32, edge 24 and a part or portion of the face 26 carrying the body of adhesive 14 will be exposed while the semi-peripheral support liner portion 34 remains attached to the backing sheet 12 to rigidify the support the dressing for handling and application. The part of the face 26 of the backing sheet exposed upon removal of the liner portion 32 includes the unsupported edge 24 as well as the final dressing portion 20; whereby the entire surface area of the final dressing 20 will be exposed. To apply the dressing to a dressing receiving surface, such as anatomical skin surface S, the dressing is grasped along the handling tab 38 and/or the semi-peripheral segment 36 without contacting or touching the exposed part of face 26. The dressing is then turned over, and edge 24 is placed against surface S as shown in FIG. 4, wherein the edge 24 is shown applied, e.g., over a venous catheter C, to be secured on surface S. The dressing is pressed against surface S to establish an adhesive bond between surface S and the exposed part of face 26 with the dressing flexing to conform to the shape of the catheter to form an adhesive seal therewith. The semi-peripheral segment 36 is manually grasped and is detached or separated from the final dressing portion 20 in one piece with a manual pulling force as shown in FIG. 5 leaving the final dressing 20 in place on the surface S.

Figure 6:
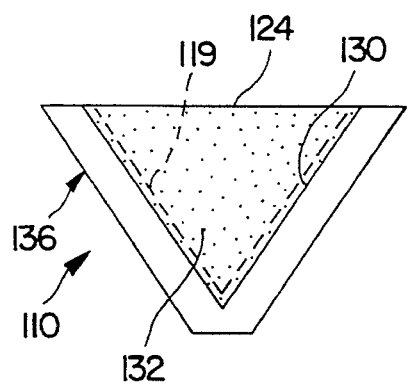
FIG. 6 is a top plan view of another embodiment of the medical dressing with semiperipheral delivery system according to the present invention.

A modification of the medical dressing with semi-peripheral delivery system according to the present invention is illustrated at 110 in FIG. 6. The medical dressing with semi-peripheral delivery system 110 is similar to the medical dressing with semi-peripheral delivery system 10 except that the backing sheet for the medical dressing with semi-peripheral delivery system 110 has triangular configuration including a V-shaped perforation line 119 not aligned with V-shaped cut line 130, the perforation line 119 being spaced inwardly of the cut line 130.

In use, the medical dressing with semi-peripheral delivery system 110 is applied on a dressing receiving surface in the same manner as that described for the medical dressing with semi-peripheral delivery system 10. Upon removal of liner portion 132, unsupported edge 124 of the final dressing 20 can be secured and anchored on the dressing receiving surface. Once the edge 124 and the exposed face of the backing sheet are applied to the dressing receiving surface, the semi-peripheral segment 136 is separated from the remainder of the dressing along perforation line 119 leaving the final dressing in place on the dressing receiving surface.

Figure 7:
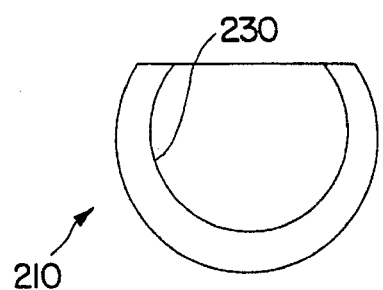
FIG. 7 is a top plan view of an additional embodiment of the medical dressing with semiperipheral delivery system according to the present invention.

FIG. 7 illustrates a medical dressing with semi-peripheral delivery system 210 having partial circular initial and final peripheral configurations with a continuously curving cut line 230 aligned with the perforation line.

By providing one or more unsupported edges of the final dressing configuration to be unconnected to the semi-peripheral segment upon removal of the removable liner portion, the present invention provides one or more final edges where no pulling force is exerted and minimizes the pulling force required when removing the semi-peripheral segment. With the present invention, the dressing can be applied via the unsupported edge(s) to a dressing receiving surface without any subsequent disturbance of the dressing during removal of the semi-peripheral segment. By allowing the unsupported edge to be anchored on the dressing receiving surface prior to removal of the semi-peripheral segment, the present invention minimizes pulling and deformation of the dressing when separating the semi-peripheral segment from the final dressing section. Unlike the prior art the present invention provides thin film support while simultaneously providing a conformal edge for sealing about an irregular surface, e.g., a catheter. Also, all of the final dressing area can be visualized prior to support removal. The semi-peripheral segment of the dressing and/or the bonding tab facilitate handling and application of the dressing without contacting the adhesive such that sterility and the integrity of the adhesive bond are not compromised. Because the semi-peripheral support liner portion remains attached to the backing sheet subsequent to removal of the removable liner portion, the backing sheet is more rigidly supported and the tendency of the backing sheet to wrinkle, buckle, fold, turn over on itself and stick together is eliminated or reduced to ensure ease of handling and proper application. The present invention requires only a single release liner disposed over the body of adhesive and thusly requires few manufacturing steps and parts and is of low cost and easy to use. The medical dressing with semi-peripheral delivery system according to the present invention can be utilized with the unsupported edge applied over a catheter to secure or stabilize the catheter with the dressing conforming to the contours of the catheter to provide an enhanced seal therewith.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A medical dressing system comprising a backing layer, an adhesive layer overlying said backing layer and a release liner overlying a skin-contacting surface of said adhesive layer, said dressing system further comprising a final dressing portion with a selectively removable release liner portion, said final dressing portion being inward of, and partially defined by, a continuous semiperipheral support portion partially surrounding said final dressing portion, said semiperipheral support portion being separable from said final dressing portion and providing support of the edges of said final dressing portion, said edges of said final dressing portion being surrounded by said continuous semiperipheral support portion such that the final dressing portion is prevented from folding upon itself during application, said final dressing portion further defined by at least one unsupported edge extending from a first to a second end of said semiperipheral support portion, which unsupported edge is substantially more comfortable than said supported edges during application.

2. The medical dressing system of claim 1 wherein said final dressing portion and semiperipheral support portion are separable, and said selectively removable release liner is removable, via a separation line.

3. The medical dressing of claim 2 wherein said separation line comprises a) a cut line extending through said release liner defining said removable liner portion and a semiperipheral liner portion; and b) a perforation line in substantial alignment with said cut line to provide for separation of said final dressing portion from said semiperipheral support portion.

4. The medical dressing system of claim 3 wherein said perforation line is slightly inward of said cut line.

5. The medical dressing system of claim 1 further including one or more handling tabs located on an outer edge of said semiperipheral support portion.

6. The medical dressing of claim 3 further including a V-groove or cut-out to facilitate initiation of detachment of said semiperipheral support portion, said V-groove or cut-out being located at the intersection of said perforation, said unsupported edge and semiperipheral support portion.

7. The medical dressing system of claim 1 wherein said backing layer is a thin conformal flexible material.

8. The medical dressing system of claim 7 wherein said backing layer is made from a material selected from the group consisting of polyurethane, copolyester, elastomeric polyester, polyethylene, blends of polyurethane and polyester, chlorinated polyethylene, styrene/butadiene block copolymers and polyvinyl chloride.

9. The medical dressing of claim 1 wherein said backing layer ranges in thickness from about 0.0005 to about 0.004 inches.

10. The medical dressing of claim 9 wherein said backing layer is from about 0.001 to about 0.002 inches in thickness.

11. The medical dressing system of claim 1 wherein said adhesive layer is a pressure sensitive adhesive suitable for use on human skin.

12. The medical dressing system of claim 11 wherein said adhesive layer is made from a material selected from the group consisting of polyurethane adhesives and acrylate copolymers.

13. The medical dressing of claim 12 wherein said polyurethane adhesives comprise a polyurethane polymer having excess hydroxyl functionality, a glass transistion temperature of less than about 0° C., a moisture vapor transmission rate of at least about 300 grams/meter$^2$/24 hours measured at 37° C. with a 90% relative humidity gradient, and a peel adhesion to human skin of between about 0.5 and 3.5 newtons/cm width of the polymer.

14. The medical dressing system of claim 1 wherein said adhesive layer is from about 0.001 to about 0.010 inches in thickness.

15. The medical dressing system of claim 1 wherein said release liner is selected from the group consisting of conventional smooth surface paper materials, polyester films and polyolefin films.

16. The medical dressing system of claim 1 wherein said release liner is at least about 0.004 inches in thickness.

17. The medical dressing system of claim 1 wherein a substantially rectangular final dressing portion of said backing, adhesive and selectively removable release liner is defined on three sides by, and separable from, a semiperipheral support portion of said backing, adhesive and remaining release liner, and defined on a fourth side by an unsupported final dressing edge extending from a first end to a second end of said semiperipheral support system.

18. The medical dressing system of claim 1 wherein said final dressing portion is substantially rectangular being about 2–6 inches wide and about 2–8 inches long and wherein said semiperipheral support portion defines and is separably attached to the outside of two intersecting or three sides and is from about 0.25 to about 0.75 inches wide.

* * * * *